United States Patent [19]

Mueller et al.

[11] Patent Number: 5,002,761
[45] Date of Patent: Mar. 26, 1991

[54] HAIR TREATMENT COMPOSITIONS CONTAINING NATURAL INGREDIENTS

[75] Inventors: Reinhard Mueller, Langenfeld; Horst Hoeffkes, Duesseldorf-Hellerhof; Kurt Seidel, Duesseldorf; Klaus-Dieter Wisotzki, Erkrath, all of Fed. Rep. of Germany

[73] Assignee: Henkel Kommanditgesellschaft auf Aktien, Duesseldorf, Fed. Rep. of Germany

[21] Appl. No.: 346,440

[22] Filed: May 2, 1989

[30] Foreign Application Priority Data

May 2, 1988 [DE] Fed. Rep. of Germany ....... 3814839

[51] Int. Cl.$^5$ ................................................ A61K 7/08
[52] U.S. Cl. ...................................... 424/70; 514/772; 514/784
[58] Field of Search .................... 424/70; 514/772, 784

[56] References Cited

U.S. PATENT DOCUMENTS

| 4,115,313 | 9/1978 | Lyon et al. | 424/70 X |
|---|---|---|---|
| 4,174,296 | 11/1979 | Kzss | 424/70 X |
| 4,314,573 | 2/1982 | Spitzer et al. | 424/70 X |
| 4,515,778 | 5/1985 | Kzstell | 424/70 X |

FOREIGN PATENT DOCUMENTS

| 179110 | 11/1982 | Japan | 424/70 |
|---|---|---|---|
| 78113 | 5/1984 | Japan | 424/70 |
| 63611 | 4/1986 | Japan | 424/70 |

Primary Examiner—Merrell C. Cashion, Jr.
Assistant Examiner—Susen S. Rucker
Attorney, Agent, or Firm—Ernest G. Szoke; Wayne C. Jaeschke; Norvell E. Wisdom, Jr.

[57] ABSTRACT

Acidic, aqueous hair treatment emulsions, in which an active ingredient combination of phospholipids of natural origin and inorganic and/or organic acids is used, improve the wet and dry combability and reduce the electrostatic charging of hair.

20 Claims, No Drawings

HAIR TREATMENT COMPOSITIONS CONTAINING NATURAL INGREDIENTS

FIELD OF THE INVENTION

This invention relates to compositions or preparations of the type generally known as hair "conditioners" or the like, intended to improve the combability of hair on a human head and to reduce its susceptibility to electrostatic charging. The compositions are formulated entirely or at least predominantly with naturally occurring ingredients, usually in the form of an aqueous emulsion.

STATEMENT OF RELATED ART

Nowadays, human hair is often subjected to a number of treatments, including washing with shampoos, in shower baths, and with bath water containing additives primarily intended to benefit the skin rather than the hair. Hair is also subjected to cosmetic procedures, such as bleaching, dyeing, or shaping. Processes such as these can cause unwanted damage to the structure of the hair, as reflected inter alia in poor wet and dry combability. In addition, the hair shows a tendency towards electrostatic charging, which adversely affects the suitability and attractiveness of hair styles.

One known possibility for overcoming these drawbacks is to subject the hair to an aftertreatment with appropriate active ingredients, generally cationic surfactants in combination with other substances. Hair aftertreatment preparations of the type in question, which are normally made up in the form of hair lotions or creamy emulsions, are described, for example in DE-OS 34 17 646, in Japanese patent specification 59/78113, and in Russian patent specification 1 090 401.

However, these hair treatment preparations have disadvantages. It is known that cationic surfactants are most suitable for the treatment of dry hair. By contrast, their use on hair which is naturally oily is problematical because they aggravate its natural oiliness. Since, in addition, cationic surfactants often irritate skin and mucous membranes, these surfactants can be used only in limited quantities in hair treatment compositions.

In addition, the quaternary ammonium compounds normally used as cationic surfactants have poor biodegradability, so that their use should be avoided as far as possible on ecological grounds.

So-called neutralizing shampoos which, in addition to large quantities of synthetic surfactants, contain phosphate esters, citric acid, and amino acids have been taught for overcoming the electrostatic charging of hair (cf. for example Cosmetics and Toiletries, Vol. 98, May 1983, page 66).

Japanese patent specification 61/238 718 describes microbicidal and anti-dandruff hair treatment preparations which may contain naturally occurring phosphorus compounds and/or organic acids and/or salts thereof as components, in addition to a synthetic microbicidal agent, in an aqueous ethanolic solution.

However, there is no reference in either of these publications to an active ingredient combination of phospholipids of natural origin and inorganic and/or organic acids or to its potential effect.

In view of the ongoing controversy over possible ill effects of synthetic chemicals, there is an increasing demand among consumers for body care preparations which consist solely of natural ingredients, i.e. substances which occur in animate or inanimate nature, and especially those which occur naturally in the human body itself.

However, the replacement of synthetic components by natural substances in body care products must not adversely affect the appearance or sensory properties of the product. Accordingly, there is also a need to provide a hair treatment preparation, based on natural active ingredient combinations, which satisfies consumer demands and expectation in its compounded form.

Accordingly, there is a need to find active ingredient combinations for hair treatment preparations which improve the wet and dry combability of hair and which reduce the static charging of hair without showing any of the disadvantages mentioned above.

DESCRIPTION OF THE INVENTION

Throughout this description, except in the operating examples or where specifically indicated to the contrary, all numbers describing quantities of ingredients or conditions of reaction or use are to be understood as modified by the word "about".

It has now surprisingly been found that the requirements stated above can be satisfied by the use of a mixture of phospholipids of natural origin with inorganic and/or organic acids as an active ingredient combination in an acidic aqueous hair treatment emulsion for improving the wet and dry combability and reducing the electrostatic chargeability of hair. At the same, it is possible, if desired, to dispense with the use of fatty alcohols, ethoxylated surfactants, and other synthetic active ingredients, and also with the usual wax and oil components. Preferred mixtures are those which contain only components which occur in nature.

According to the invention, it is preferred to use hair treatment emulsions containing from 0.1 to 20% by weight and more preferably from 1 to 3% by weight of a natural phospholipid, from 0.1 to 20% by weight and more preferably from 1 to 3% by weight of an inorganic acid and/or organic acid, and from 0.01 to 2% by weight and more preferably from 0.05 to 0.5% by weight of an additional emulsifier.

In addition, the components of the active ingredient combination, i.e. the phospholipid and the inorganic and/or organic acid, are preferably present in the hair treatment emulsion in a ratio by weight of from 2:1 to 1:2.

Preferable natural phospholipids are lecithins, such as egg lecithin and soya lecithin. However, kephalins may also be used effectively as a phospholipid component of the composition according to the invention.

Both inorganic and organic acids may be used as the acid component of the active ingredient combination. It is preferred to use acids which also occur in nature. Suitable inorganic acids are, for example, phosphoric acid, sulfuric acid, and hydrochloric acid. Among the organic acids, those containing from 1 to 12 carbon atoms are preferred. There is a particular preference for edible acids, i.e., organic acids which have positive effects on the human organism in the context of normal food uptake. Examples of such acids are acetic acid, lactic acid, tartaric acid, citric acid, malic acid, ascorbic acid, and gluconic acid. Citric acid and ascorbic acids are particularly preferred as acid components of the active ingredient combination according to the invention.

The acidic hair treatment emulsions are preferably adjusted to a pH value of from 2 to 6 and more preferably to a pH value of from 2.5 to 4.5. Emulsions having a pH value in the range from 2.5 to 3.5 show particularly good properties. The pH value is adjusted by means of the type and quantity of acids used and, optionally, by the further addition of a base, for example, an alkali metal hydroxide or an amine, such as triethanolamine. A buffering effect, i.e., pH stabilization of the emulsion in the adjusted pH range, can be obtained by the acid/base combination.

Since, in contrast to the acids, the phospholipids used are insoluble in water, the active ingredient combination used cannot be prepared in the form of a clear aqueous solution. The use of mixtures of water and watersoluble alcohols, such as for example ethanol or isopropanol, as a common solvent for the active ingredient combination is attended by the disadvantage that the large quantities of alcohol required to obtain a clear solution can lead to irritation of the scalp.

However, it has been found that the emulsifying properties of the phospholipids used are normally sufficient to enable the active ingredient combination to be made up in the form of an aqueous emulsion.

Nevertheless, it is possible to increase the stability of the emulsion, particularly with a view to prolonging potential shelf life, by the addition of other emulsifiers. The consistency of the emulsion may also be regulated as required through these emulsifiers. So far as the emulsifiers are concerned, it is again preferred to use compounds which also occur in nature.

Known natural emulsifiers include, for example, bile acids, among which cholic acid, deoxycholic acid and lithocholic acid and—as a derivative of cholic acid—taurocholic acid are noted in particular. Tannic acid, abietic acid, and saponins are other suitable emulsifiers.

The acids mentioned may be used as free acids. However, it is also possible to use the corresponding alkali salts, particularly the lithium, sodium, or potassium salt, or the ammonium salt. These salts may be obtained in known manner by reaction of the corresponding acids with the particular alkali carbonates, alkali hydrogen carbonates or ammonia. In general, the salts have better emulsifying properties than the free acids. Among the alkali salts, emulsifying power increases in the order lithium, sodium, potassium. Accordingly, it is particularly preferred to use potassium salts, particularly the potassium salt of cholic acid, as an additional emulsifier.

It is known among those skilled in the art that the viscosity of an aqueous emulsion can be controlled by addition of so-called thickeners. Accordingly, the emulsions according to the invention may contain from 0.1 to 10% by weight and more especially from 0.5 to 5% by weight of a thickener to obtain a viscosity suitable for application. Emulsions having viscosities in the range from 2,500 to 4,000 millipascal seconds (mPa.s) and more especially in the range from 3,000 to 3,500 mPa.s at 20° C. are particularly preferred for hair rinses. By contrast, emulsions having viscosities in the range from 10,000 to 100,000 mPa.s are normally used for hair treatment emulsions which are marketed as so-called hair "creams".

Once again, it is preferred to use thickeners which occur in nature. Thickeners such as these include polysaccharides, more especially xanthan gum, guar gum, agar agar, alginates, carob bean flour, and pectins.

The acidity of the hair treatment emulsion has a positive effect on its stability. In addition, some of the acids used as active ingredient component have preserving properties of their own which are sufficient for normal use. However, other preservatives may also be added to an emulsion in accordance with the invention. Suitable preservatives are, for example, salicylic acid, formic acid, propionic acid, benzoic acid, sorbic acid, cinnamic acid, menthol, thymol, eugenol, and lemon grass extract. These preservatives are preferably used in quantities of from 0.1 to 2% by weight in the hair treatment emulsion. The use of benzoic acid as a preservative is particularly preferred.

The emulsions according to the invention may additionally contain other conventional constituents of hair treatment preparations known to those skilled in the art, in quantities of at most 5% by weight. Such constituents include, for example, dyes; perfumes; surfactants; antioxidants; light stabilizers; hair nourishing agents, such as vitamins, plant extracts, and balsams; antidandruff agents or sebostatic agents; oil components, preferably natural vegetable and animal oils and fats; and waxes.

The following operating examples are intended to illustrate the invention without limiting it in any way.

EXAMPLES 1–9

The hair treatment emulsions listed in Table 1 below were prepared as follows:

The tabulated phospholipid, acid, and additional emulsifier were melted and mixed while melted at 70° to 80° C. The preservative, dissolved in approximately 65 parts by weight of hot water, was then added with vigorous stirring to the mixture of lipid, acid, and emulsifier. After cooling of the mixture with vigorous stirring to around 45° C., the thickener was added in the form of a water swollen mass with the remaining water. Light yellow, fine emulsions were formed in each case. In the case of Examples 1 and 2, the emulsions were adjusted to the desired pH value by addition of an appropriate quantity of triethanolamine.

The viscosity values shown were determined using a Brookfield RVF viscosimeter, spindle 4, at 20 revolutions per minute.

The hair treated with emulsion according to Example 1 showed satisfactory wet and dry combability and slightly reduced electrostatic charging. Good wet and dry combability and distinctly reduced electrostatic charging were obtained by treating the hair with emulsion according to Example 2. The treatment of hair with emulsions according to Examples 3 to 9 produced very good wet and dry combability. In addition, the hair thus treated showed virtually no electrostatic charging.

TABLE 1

| SPECIFICS OF COMPOSITIONS OF THE OPERATING EXAMPLES | | | | | | | | | |
|---|---|---|---|---|---|---|---|---|---|
| | Parts by Weight of Constituent in Composition of Example No.: | | | | | | | | |
| Constituents | 1 | 2 | 3 | 4 | 5 | 6 | 7 | 8 | 9 |
| Phospholipid | | | | | | | | | |
| soya lecithin | 1.7 | 1.7 | 2.5 | 4.0 | 1.7 | — | 1.7 | 1.68 | 2.5 |
| egg lecithin | — | — | — | — | — | 1.7 | — | — | — |
| Acid | | | | | | | | | |
| citric acid | 1.7 | 1.7 | 1.7 | 4.0 | 2.4 | 1.7 | — | — | — |

TABLE 1-continued

SPECIFICS OF COMPOSITIONS OF THE OPERATING EXAMPLES

| Constituents | Parts by Weight of Constituent in Composition of Example No.: | | | | | | | | |
|---|---|---|---|---|---|---|---|---|---|
| | 1 | 2 | 3 | 4 | 5 | 6 | 7 | 8 | 9 |
| lactic acid | — | — | — | — | — | — | — | — | 1.7 |
| malic acid | — | — | — | — | — | — | 1.7 | — | — |
| phosphoric acid | — | — | — | — | — | — | — | 1.68 | — |
| Emulsifier | | | | | | | | | |
| cholic acid, $Na^+$ salt | 0.1 | 0.1 | — | — | — | 0.1 | — | 0.1 | — |
| cholic acid, $K^+$ salt | — | — | — | — | 0.1 | — | — | — | — |
| cholic acid | — | — | — | — | — | — | — | — | 0.5 |
| saponin | — | — | 0.5 | — | — | — | — | — | — |
| taurocholic acid, $Na^+$ salt | — | — | — | 0.2 | — | — | — | — | — |
| deoxycholic acid | — | — | — | — | — | — | 0.1 | — | — |
| Thickener | | | | | | | | | |
| xanthan gum | 1.0 | 1.0 | 1.0 | 1.0 | — | 1.0 | 1.0 | 1.0 | 1.0 |
| Na alginate | — | — | — | — | 3.5 | — | — | — | — |
| Preservative | | | | | | | | | |
| benzoic acid | 0.5 | 0.5 | 0.4 | — | 0.5 | 0.3 | 0.3 | 0.5 | 0.4 |
| sorbic acid | — | — | — | 0.4 | — | — | — | — | — |
| Water | 95 | 95 | 93.9 | 90.4 | 90.2 | 95.2 | 95.2 | 95.04 | 93.9 |
| Triethanolamine | to pH 5.9 | to pH 4.1 | — | — | — | — | — | — | — |
| Glucose | — | — | — | — | 2.0 | — | — | — | — |
| pH value | 5.9 | 4.1 | 3.2 | 3.0 | 3.1 | 2.4 | 2.5 | 2.0 | 2.9 |
| Viscosity (mPa · s) at 20° C. | — | — | 3000 | 3500 | 3950 | 3500 | 3650 | 3850 | 4600 |

What is claimed is:

1. An aqueous hair conditioner emulsion comprising (A) water, (B) phospholipid or phospholipids of natural origin, and (C) acid or acids selected from the group consisting of inorganic acid, acetic acid, lactic acid, tartaric acid, citric acid, malic acid, ascorbic acid, gluconic acid, and mixtures thereof, in an amount to give the emulsion a pH value between about 2.5 and about 6.

2. An emulsion according to claim 1, wherein the amount of component (B) is from about 0.1 to about 20% by weight, the amount of component (C) is from about 0.1 to about 20% by weight, and the emulsion contains from about 0.1 to about 2% by weight of additional emulsifier or emulsifiers as component (D).

3. An emulsion according to claim 2, wherein the amount of component (B) is from about 1 to about 3% by weight, the amount of component (C) is from about 1 to about 3% by weight, the amount of component (D) is from about 0.05 to about 0.5% by weight, and component (D) consists of materials found in nature.

4. An emulsion according to claim 2, having a pH value in the range from about 2.5 to about 4.5.

5. An emulsion according to claim 3, having a pH value in the range from about 2.5 to about 3.5.

6. An emulsion according to claim 2, wherein the ratio by weight between component (B) and (C) is from about 2:1 to about 1:2.

7. An emulsion according to claim 2, wherein component (B) is selected from lecithins and kephalins.

8. An emulsion according to claim 7, wherein component (B) is selected from egg lecithin, soya lecithin, and mixtures thereof.

9. An emulsion according to claim 2, wherein component (C) is selected from the group consisting of phosphoric acid, sulfuric acid, hydrochloric acid, acetic acid, lactic acid, tartaric acid, citric acid, malic acid, ascorbic acid, gluconic acid, and mixtures thereof.

10. An emulsion according to claim 9, wherein component (C) is selected from the group consisting of acetic acid, lactic acid, tartaric acid, citric acid, malic acid, ascorbic acid, gluconic acid, and mixtures thereof.

11. An emulsion according to claim 3, wherein component (C) is selected from the group consisting of citric acid, ascorbic acid, and mixtures thereof.

12. An emulsion according to claim 2, wherein component (D) is selected from the group consisting of (i) cholic acid, lithocholic acid, deoxycholic acid, taurocholic acid, tannic acid, and abietic acid; (ii) alkali metal and ammonium salts of the acids in group (i); (iii) saponins; and (iv) mixtures of any of the above.

13. An emulsion according to claim 3, wherein component (D) is selected from the group consisting of the alkali metal and ammonium salts of cholic acid, lithocholic acid, deoxycholic acid, taurocholic acid, tannic acid, and abietic acid, and mixtures of any of these salts.

14. An emulsion according to claim 2, additionally comprising between about 0.1 and about 10% by weight of thickener.

15. An emulsion according to claim 3, additionally comprising between about 0.1 and about 10% by weight of a thickener selected from the group consisting of xanthan gum, guar gum, agar agar, alginates, carob bean flour, pectins, and mixtures thereof.

16. An emulsion according to claim 6, additionally comprising between about 0.5 and about 5% by weight of a thickener selected from the group consisting of xanthan gum, guar gum, agar agar, alginates, carob bean flour, pectins, and mixtures thereof.

17. An emulsion according to claim 2, comprising at least one additional preservative.

18. An emulsion according to claim 3, additionally comprising a preservative selected from the group consisting of menthol, thymol, eugenol, lemon grass extract, and mixtures of any of these.

19. An emulsion according to claim 2, comprising a preservative-effective amount of benzoic acid.

20. A method for treating human hair to decrease its tendency to become electrostatically charged by combing and brushing, comprising contacting the hair with an aqueous hair conditioner emulsion comprising (A) water, (B) phospholipid or phospholipids of natural origin, and (C) acid or acids selected from the group consisting of inorganic acids, acetic acid, lactic acid, tartaric acid, citric acid, malic acid, ascorbic acid, gluconic acid, and mixtures thereof, in an amount to give the emulsion a pH value between about 2.5 and about 6.

* * * * *